United States Patent
Rezai Jahromi et al.

(10) Patent No.: US 11,266,419 B2
(45) Date of Patent: Mar. 8, 2022

(54) DEVICE FOR APPLYING EXTERNAL PRESSURE ON A SURFACE OF AN ANATOMICAL OBJECT

(71) Applicant: HELSINKI SURGICAL INSTRUMENTS AB, Helskinki (FI)

(72) Inventors: Behnam Rezai Jahromi, Helsinki (FI); Valdemar Hirvela, Helsinki (FI); Stepan Sarpaneva, Helsinki (FI); Juha Hernesniemi, Helsinki (FI)

(73) Assignee: Helsinki Surgical Instruments AB, Helsinki (FI)

( * ) Notice: Subject to any disclaimer, the term of this patent is extended or adjusted under 35 U.S.C. 154(b) by 70 days.

(21) Appl. No.: 16/650,089

(22) PCT Filed: Sep. 29, 2017

(86) PCT No.: PCT/FI2017/050690
§ 371 (c)(1),
(2) Date: Mar. 24, 2020

(87) PCT Pub. No.: WO2019/063871
PCT Pub. Date: Apr. 4, 2019

(65) Prior Publication Data
US 2020/0229822 A1 Jul. 23, 2020

(51) Int. Cl.
*A61B 17/122* (2006.01)

(52) U.S. Cl.
CPC ........ *A61B 17/122* (2013.01); *A61B 17/1227* (2013.01)

(58) Field of Classification Search
CPC ....... A61B 17/08; A61B 17/083; A61B 17/12; A61B 17/122; A61B 17/1227;
(Continued)

(56) References Cited

U.S. PATENT DOCUMENTS

| 5,454,826 A | 10/1995 | Ueda |
| 6,179,850 B1 | 1/2001 | Goradia |

(Continued)

FOREIGN PATENT DOCUMENTS

| CN | 202568357 U | 12/2012 |
| CN | 103126740 A | 6/2013 |

(Continued)

OTHER PUBLICATIONS

International Search Report for PCT/FI2017/050690 dated Jan. 24, 2018.

(Continued)

*Primary Examiner* — Melanie R Tyson
(74) *Attorney, Agent, or Firm* — Thomas|Horstemeyer LLP

(57) ABSTRACT

A device for applying external pressure on a surface of an anatomical object, such as a blood vessel, includes at least two jaws, a closing force generating device for applying compressive or closing force to the jaws so to driving the jaws against each other. The device also includes an actuating device for applying counterforce against the compressive force, and a control unit. The control unit controls the operation of the actuating device to apply the counterforce so that the external pressure applied by the jaws into the surface of the anatomical object, such as a blood vessel, is applied in a way to manipulate a flow rate of a fluid circulation in the anatomical object as a function of time in a controllable manner.

21 Claims, 3 Drawing Sheets

(58) Field of Classification Search
CPC ....... A61B 17/132; A61B 17/28; A61B 17/29; A61B 2017/12004; A61B 2017/2808
See application file for complete search history.

(56) References Cited

U.S. PATENT DOCUMENTS

| | | |
|---|---|---|
| 2011/0022062 A1 | 1/2011 | Hegemann et al. |
| 2013/0338688 A1 | 12/2013 | Rehman et al. |

FOREIGN PATENT DOCUMENTS

| | | |
|---|---|---|
| CN | 203001029 U | 6/2013 |
| CN | 203736255 U | 7/2014 |
| DE | 10261937 A1 | 10/2004 |
| WO | 2004071275 A2 | 8/2004 |
| WO | 2009048379 A2 | 4/2009 |
| WO | 2009048379 A3 | 5/2009 |
| WO | 2012048387 A1 | 4/2012 |
| WO | 2013009623 A2 | 1/2013 |

OTHER PUBLICATIONS

European Search Report for Application No. 17927192.9 dated Mar. 15, 2021.

DEVICE FOR APPLYING EXTERNAL PRESSURE ON A SURFACE OF AN ANATOMICAL OBJECT

CROSS-REFERENCE TO RELATED APPLICATIONS

This application is the 35 U.S.C. § 371 national stage application of PCT Application No. PCT/FI2017/050690, filed Sep. 29, 2017, which is herein incorporated by reference in its entirety.

TECHNICAL FIELD OF THE INVENTION

The invention relates to a device for applying external pressure on a surface of an anatomical object. The anatomical object may any anatomic fluid channel of an animal or human, such as a blood vessel.

BACKGROUND OF THE INVENTION

Many anatomical objects of human and animal body are objected to manipulation, such as compression e.g. during surgical operations. Often these anatomical objects have anatomic fluid channels, such as blood vessels or intestine, the flow of which should be manipulated or even prevented completely during or after the operation. Sometime these operations are called as a flow modulation surgery, where the fluid flow in the anatomical objects must be reduced or limited or otherwise manipulated.

Dolichoectatic basilar trunk aneurysms or non-saccular aneurysms are one of the most challenging surgical problems that any surgeon will encounter, where the surgical intervention is to relieve symptoms or to prevent aneurysm progression e.g. by flow modulation surgery, such as by changing hemodynamic stress of the artery. The treatment of dolichoectatic basilar trunk aneurysms has still been ineffectual or morbid due to non-saccular morphology, deep location, and involvement of brainstem perforators. Treatment with bypass surgery has been advocated to eliminate malignant hemodynamics and to stabilize aneurysm growth.

Progressive structural and morphological changes in the arterial walls are accompanied by hemodynamic changes, generating regions of abnormal flow velocity, wall shear stress, turbulence, and stagnation, which in turn might exacerbate arterial degeneration through degradation, thrombus formation, and inflammation If the hemodynamic stress exceeds the strength of the aneurysm wall the aneurysms will rupture. According to known methods a vascular anomaly, such as a dolichoectatic aneurysm, arteriovenous malformation, dural arteriovenous fistula or fusiform aneurysm, is isolated from the blood circulation or, at least, the flow and flow-induced mechanical stress is reduced in the vascular anomaly, such as in the aneurysm sac, which would prevent it from growing or bleeding and cure the disease, as is the case with more common saccular aneurysms.

Treatment of dolichoectatic basilar trunk aneurysms with bypass surgery has been advocated as a means of eliminating malignant hemodynamics, redirecting flow away from areas of aneurysmal degeneration, and promoting intraluminal thrombosis, thereby stabilizing aneurysm growth and preventing hemorrhage.

Different kinds of clips are used for isolating the aneurysms from the blood circulation or reducing the blood flow in the blood vessel in the contact with the aneurysm. For example clip occlusion of the basilar artery, whether distal or proximal, eliminates basilar flow except what its branches can pull or sump either from the proximal basilar artery in the case of distal aneurysm occlusion or from the bypass in the case of proximal aneurysm occlusion. Small perforating branches are unable to sump enough flow for their preservation and are overwhelmed by stagnation of blood within a vast intra-aneurysmal space, leading to thrombosis.

However the end results when using the clips, for example, depend on sufficient but not too significant reduction in blood flow, namely too small reduction in flow will not be sufficient to prevent aneurysm growth and subsequent progression in symptoms. The known clips have a drawback that they often presses the anatomical object, such as the blood vessel, too strongly or too weakly, and in addition with a certain constant force. In addition the closing time of the blood vessel is very important but challenging to estimate especially when using the clips. Typically the closing time of the blood vessel should be slow enough so that the biology involved in an environment of the blood vessel can revive and integrate to the new conditions, but fast enough in order to prevent aneurysm progression. The previous experiences are associated with significant morbidity and no clear solution has been demonstrated.

SUMMARY OF THE INVENTION

An object of the invention is to alleviate and eliminate the problems relating to the known prior art. Especially the object of the invention is to provide a device for applying external pressure on a surface of an anatomical object, such as a blood vessel, so that the compression force and/or the closing time of the anatomical object or flow inside the anatomical object is slow enough so that e.g. the biology involved in an environment of the anatomical object can revive and integrate to the new conditions, but fast enough in order to prevent any further symptoms or drawbacks.

The object of the invention can be achieved by the features of independent claims.

The invention relates to a device according to claim 1.

According to an embodiment of the invention a device for applying external pressure on a surface of an anatomical object, such as a blood vessel, is provided. An example of the anatomic object is a blood vessel, but the anatomic object may also be some other fluid channel of an animal or human, such as intestine or the like. The device comprises at least two jaws, which can be clamped against each other either completely or at least a certain distance e.g. so that a certain space is left between the jaws. According to an embodiment the jaws can also be removed farther from each other. However this is an optional feature.

The device comprises also a closing force generating device for applying compressive or closing force to the jaws so to driving the jaws against each other, but not necessarily to close to each other. The closing force generating device may be e.g. a spring mechanically coupled with the jaws and applying force driving the jaws against each other. For example the device with the jaws can be manufactured so that the jaws are made from the same piece of material so that the structure of the jaws or a hinge portion of the jaws induces said closing force. However these are only examples and also other implementations can be used, as is described elsewhere in this document.

In addition the device comprises also an actuating device for applying counterforce against the compressive force, and a control unit. The control unit controls the actuating device to apply the counterforce so that the external pressure applied by the jaws on the surface of said anatomical object, such as blood vessel, is applied in a way to manipulate a flow rate of the fluid circulation, such as the blood circulation, in the anatomical object in a controllable manner. For example the manipulation may be implemented so that the closing speed of the jaws and/or force applied by the jaws is predetermined or otherwise controlled, such as in real time based on a measurement results, for example. For example compressing force or flow rate of the fluid flow in the anatomical object can be measured and the measuring information being response to said compressing force or flow rate can be used as control information in order to increase or decrease the counterforce and thereby decreasing or increasing the flow rate of the fluid inside the anatomical object.

According to an embodiment the actuating device may comprise a cylinder and piston, where the piston is arranged to apply the counterforce. The piston is advantageously arranged between the jaws, whereupon it can directly mechanically prevent the jaws to be clamped against each other freely. The cylinder advantageously comprises fluid inside the cylinder to prevent the piston to move freely inside the cylinder. The control unit is configured to remove the fluid from the cylinder in a controlled manner and thereby allowing the piston to be retreated inside the cylinder and again thereby manipulating, such as decreasing, the counterforce and allowing the jaws to be driven against each other in a controlled manner.

As an example the device may comprise a valve being coupled with the cylinder so that the fluid from the cylinder can be led out via the valve. The control unit advantageously controls the operation of the valve and thereby controls the removing of the fluid outside from the cylinder via the valve and again thereby manipulating, such as decreasing, the counterforce and allowing the jaws to be driven against each other in a controlled manner. The system may be implemented e.g. by a microcontroller and micro-valve (MEMS/Microelectromechanical systems technology).

According to an embodiment a small amount of the fluid can be removed or let out from the cylinder from time to time, whereupon the spring or other closing force generating device can press the jaws again against the blood vessel or other anatomical object. The closing time of the jaws and thereby closing time of the blood vessel can be predetermined, like a week, month or the like. As an example the control unit may be programmed or there can be a map about the closing speed and closing time, possibly also about the pressing force by which the jaws are pressing the blood vessel. In addition according to an example the closing parameters can be changed during operation, advantageously outside in a contactless manner, such as by using wireless communication technologies. Naturally also wired communication technologies can be used. In addition it is to be noted that the closing speed may be linear or non-linear or having a special closing function in a time, depending on the purpose and need of the application.

According to another embodiment the valve can be replaced by a screw conveyor, which is arranged in connection of said fluid inside the cylinder. The fluid may be e.g. gel. In this embodiment the control unit controls the operation of the screw conveyor and thereby the removing of the fluid outside from the cylinder by using the screw conveyor and again thereby manipulating, such as decreasing, the counterforce and allowing the jaws to be driven against each other in a controlled manner.

According to an embodiment the cylinder may comprise fluid inside the cylinder in both a first and second side of the piston. In this embodiment the piston is moved inside the cylinder only if the fluid is removed from the first side of the cylinder and at the same time feed to the second side of the cylinder under the control of the control unit. By this the closing of the jaws can be prevented for safety in the case when there is only one valve used and if it tends to leak.

The actuating device for applying counterforce against the compressive force can also be implemented in other ways. For example the actuating device may be an electrically driven motor the output of which is mechanically coupled to at least one of the jaws to apply the counterforce so that the external pressure applied by the jaws on the surface of the anatomical object is applied in a way to manipulate, such as decrease or increase, the flow rate of the fluid circulation in the anatomical object in a controllable manner. The mechanical coupling may be implemented e.g. via a screw or threaded rod, for example, but also other methods can also be used. The electrically driven motor may be e.g. a micromotor, piezoelectric motor, rowball mechanism me or DC-motor, and in addition it may be driven 2-way, whereupon the counterforce can be decreased or increased and whereupon the compressive force can be increased or decreased, respectively.

According to an embodiment the device may also comprise a pressure accumulator, which can apply additional counterforce for example via the actuating device or the valve advantageously in a controlled manner and thereby moving the jaws farther from each other and decreasing the external pressure applied by the jaws on the surface of the object. The pressure accumulator may be connected with the cylinder and piston via a conduit so that when manipulated it extruded the piston from the cylinder and thereby moves the jaws farther from each other. This can be for example for safety reason if the effect of the compressive force should be stopped suddenly. Of course the pressure accumulator conduit can be provided with a valve, which can be operated e.g. by the control unit so that the pressure can be led from the pressure accumulator via the conduit to the cylinder to extrude the piston in a controlled manner. The control commands may be provided outside the device in a wireless or wired manner, or the device itself may determine flow rate or flow velocity or pressure by which the anatomical object is pressed or other parameter and use that information as a control information in order to control the counterforce.

The device may comprise a pressure and/or force sensor for determining pressure and/or force by which the jaws are pressed against the anatomical object. The device may also comprise a flow rate or flow velocity measuring device for determining flow rate or flow velocity of the fluid flowing inside said anatomical object. The flow rate or flow velocity measuring device may be implemented e.g. by an infrared sensor or ultrasound sensor. In addition the diameter or dimensions of the anatomical object can be determined e.g. the opening angle of the jaws or distance between the jaws.

According to an example the control unit can use the determined pressure and/or force information, as well as flow rate or velocity information and other information as a control parameter to control the actuating device to apply the counterforce so that the external pressure applied by the jaws on the surface of the anatomical object, such as the blood vessel, is applied in a way to manipulate the flow rate of the fluid circulation in the anatomical object in a controlled manner, and especially determined manner. For example if the flow rate should be decreased in a certain speed the device may determine the current flow rate and determine also the trend whether the flow rate is decreased as planned. If the flow rate or trend shows e.g. too slow decreasing, the control unit can control the actuating device to apply smaller counterforce, thereby allowing the jaws to be pressed more tightly against each other and the anatomical object, and again thereby manipulate the flow circulation so to fasten the decreasing of the flow rate. The manipulation is performed advantageously as a function of time and in a controllable manner, for example in a predetermined manner.

Still in addition the device may also comprise a transmitter to transmit information related to control unit or control parameters or determined pressure, compressing force (which is equal to counterforce in a balance) or distance information about the distance between the jaws (so diameter or thickness of the anatomic object between the jaws) or information about the opening angle of the jaws outside the device. The device may also comprise a receiver device for receiving data outside the device, such as receiving control data to be used by the control unit for controlling the operation of the actuating device. For example when the anatomic object or a symptom, such as aneurysms, is e.g. imaged or otherwise its condition or state is determined, possible new control data with new parameters can be provided based on the image or other determination information, such as determined hemodynamic. The new control data with new parameters may relate for example to closing operations, and for example the closing operation can be interrupted e.g. for a while and then continued after a certain time slot. The new control data with new parameters can then be transmitted to the receiver and again for the control unit.

The data communication between the transmitter and the external device, as well as between the receiver and the external device can be implemented either in a wired way or wireless, such as using short range radio frequencies or infrared communication techniques.

The device may also comprise a memory device to store e.g. control data so that the control unit has access to the memory device and the data stored thereon, and use the control data as to operate the actuating device and thereby controlling the closing or optionally also opening parameters of the jaws, such as the closing speed and time of the jaws so that the external pressure applied by the jaws on the surface of the anatomical object manipulates, such as decreases or increases the flow rate of the fluid circulation in the anatomical object according to said control data. It is to be noted that the closing time of the jaws can be e.g. linear or non-linear or according to a certain pattern or formula, such as faster at the beginning and then slower. In addition it is to be noted that the control data or other information may be stored to the memory device either beforehand so before introducing the device with the anatomical object or it may be transmitted to the memory device also afterwards by the communication methods described elsewhere in this document. Still the control data or other information may be permanently stored or it can be rewritten. The memory device may be implemented e.g. by a flash memory or other suitable memory devices known by the skilled person.

The device may also comprise a clockwork device providing a timing parameter to the control unit to control actuating parameters of the actuating device according to the timing parameter and possibly together with other control parameters, and thereby controlling the closing parameters of the device, such as the closing speed and time of the jaws so that the external pressure applied by the jaws on the surface of said anatomical object manipulates the flow rate of fluid circulation in the anatomical object as a function of time according to the timing parameter provided by the clockwork device. For example the control data may have information about the closing or opening speed of the jaws as a function of time, whereupon the control unit receives the timing parameter and manipulates the actuating device according to the control data as a function of time.

The device may comprise a self-reset function for resetting the parameters. The parameters can be reset for example in the case the control unit is in a malfunction state or when triggered outside the device.

According to embodiments of the invention the distal end of at least one of the jaw is curved or it comprises a serrated or friction surface so to prevent the anatomical object, such as a blood vessel, to slip away between the jaws during the operation and especially when applying compressive force. The distal end of at least one of the jaw may also comprise a hole to allow to stich at least a portion of the anatomical object to the device in order to prevent the anatomical object to slip away between the jaws.

The device can naturally be manufactured of different materials, such as essentially of titanium, which is very advantageous in order to prevent it to interfere e.g. MRI scanning. Also other materials can be used, such as ceramic materials.

Depending on the application the material of the device or jaws, for example, can vary. Also the compressive force of the jaws against each other can be selected to be suitable for intended use or application and varies typically between the range of 0.1-50 N. For example for smaller blood vessel the compressive force of the jaws is in the region of 1-5 N, more advantageously around 2 N. According to an embodiment the magnitude of the compressive force is adjustable, such as a spring which length can be adjusted thereby adjusting the magnitude of the compressive force.

The present invention offers advantages over the known prior art, such as applying external pressure on a surface of an anatomical object, such as a blood vessel, so that the compression force and/or the closing time of the anatomical object or flow inside the anatomical object is slow enough so that e.g. the biology involved in an environment of the anatomical object can revive and integrate to the new conditions, but fast enough in order to prevent any further symptoms or drawbacks. Most advantageously the closing parameters can be programmed beforehand suitable for the current operation or even controlled during the operation e.g. based on the measurement data. In addition the device of the invention can also provide a safety function namely the closing operation can be interrupted e.g. for a while if there exist any anomalies during operation and then continued after a certain time slot, or the jaws can be even opened if the effect of the compressive force should be stopped suddenly for any reason.

In particularly the manipulation time of the anatomic object, such as the closing time of the blood vessel, can be manipulated or controlled so that biological responses of the objects involved in the environment of the anatomical object can be controlled or manipulated by manipulating the flow rate of the fluid inside the anatomic object in question. For example the device according to the embodiment of the invention can be used for applying external pressure on a blood vessel in a brain and thereby changing hemodynamic stress and hemodynamic flow by changing arterial or venous diameter to achieve wanted hemodynamic changes in arterial and venous system, as an example.

The exemplary embodiments presented in this text are not to be interpreted to pose limitations to the applicability of the appended claims. The verb "to comprise" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which.

DETAILED DESCRIPTION

Figure 1:
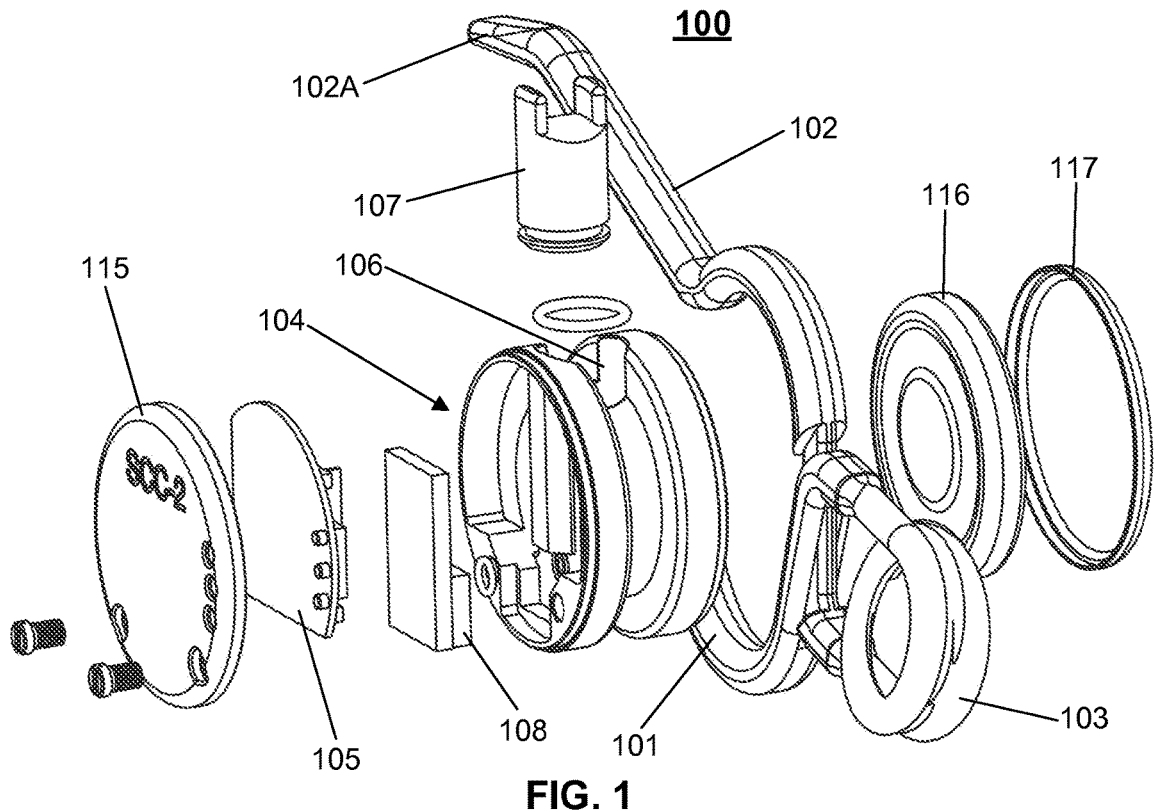
FIG. 1 illustrates an exploded view of an exemplary device for applying external pressure on a surface of an anatomical object according to an advantageous embodiment of the invention.
Figure 2:
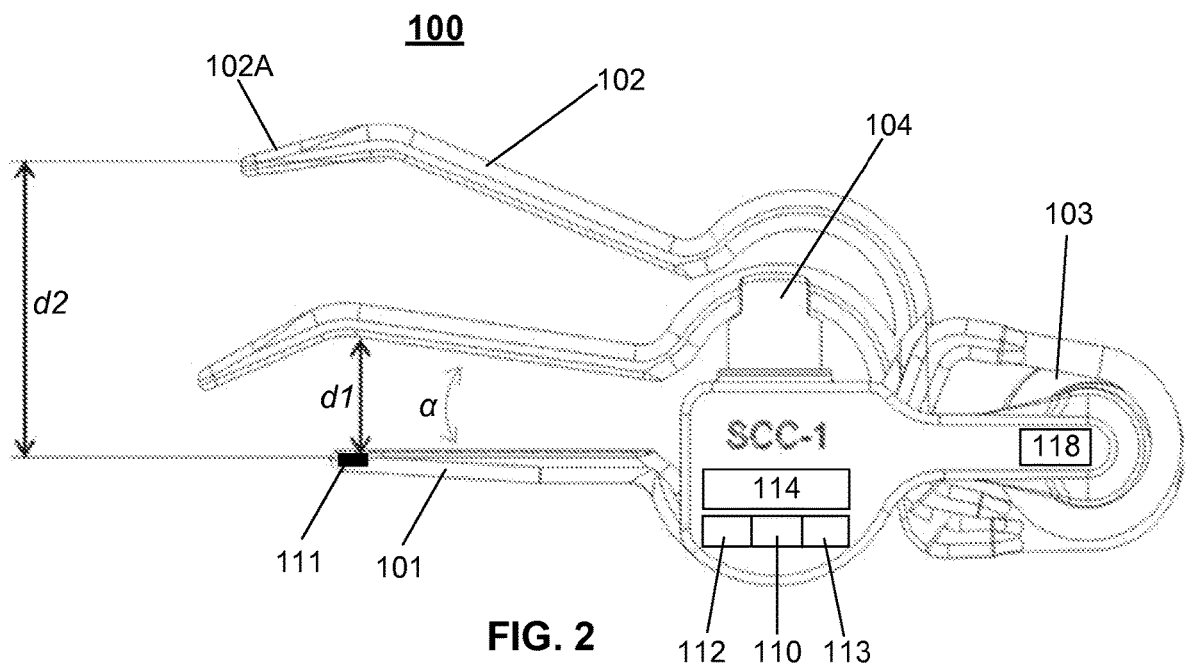
FIG. 2 illustrates a side view of an exemplary device for applying external pressure on a surface of an anatomical object according to an advantageous embodiment of the invention.
Figure 3:
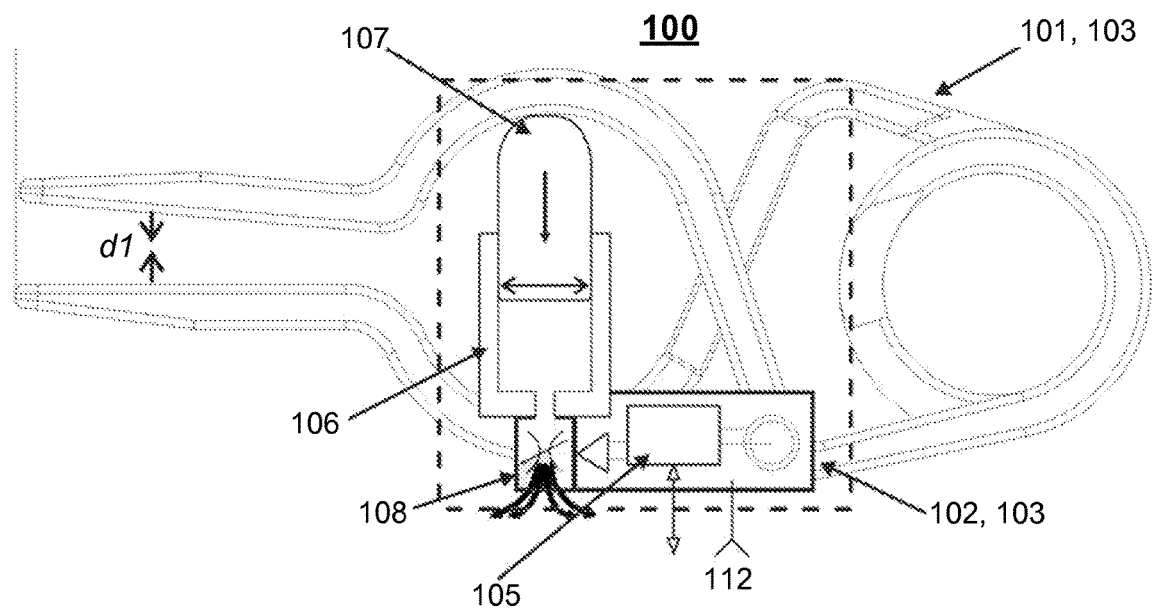
FIG. 3 illustrates additional side view of an exemplary device according to an advantageous embodiment of the invention.

FIGS. 1-6 illustrate examples of a device 100 for applying external pressure on a surface of an anatomical object according to an advantageous embodiment of the invention, where the device 100 comprises at least two jaws 101, 102. The jaws 101, 102 can be clamped against each other either completely or at least a certain distance d1, d2 e.g. so that the space is left between the jaws for receiving the anatomical object.

The device comprises also a closing force generating device 103 for applying compressive or closing force to the jaws 101, 102, such as a spring. As can be seen in Figures the device with the jaws is advantageously manufactured so that the jaws are made from the same piece of material so that the structure as such provides the spring 103 in the hinge portion of the jaws and thereby induces the closing force. Naturally also other implementation as the closing force generating device 103 can be used for providing suitable closing force.

The device comprises also an actuating device 104 for applying counterforce against the compressive force, and a control unit 105 for controlling the operation of the actuating device 104. In the embodiments illustrated especially in FIGS. 1 and 3 the actuating device 104 comprises a cylinder 106 and piston 107, where the piston 107 is arranged between the jaws 101, 102. When arranged between the jaws 101, 102 the actuating device 104, or the piston 107, directly mechanically prevents the jaws to be clamped against each other freely. According to an example the cylinder 106 comprises fluid inside the cylinder to prevent the piston to move freely inside the cylinder. The control unit 105 controls the removing the fluid from the cylinder in a controlled manner and thereby allowing the piston 107 to be retreated inside the cylinder and again thereby manipulating, such as decreasing, the counterforce and allowing the jaws 101, 102 to be driven against each other in a controlled manner.

The device comprises also a valve 108, which is coupled with the cylinder 106 so that the fluid from the cylinder can be led out via the valve 108 under the operation of the control unit 105.

Figure 4:
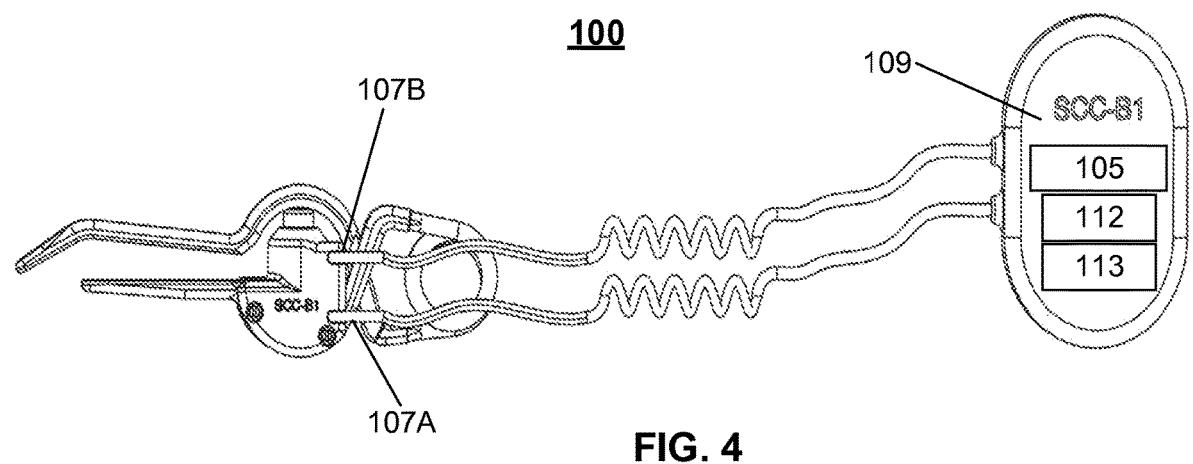
FIG. 4 illustrates another exemplary device according to an advantageous embodiment of the invention.

The fluid circulation can also be implemented so that the cylinder 107 may comprise fluid inside the cylinder in both a first and second sides 107A, 107B of the piston 107, as is the case with the device illustrated in FIG. 4, for example. In this embodiment the piston 107 is moved inside the cylinder only if the fluid is removed from the first side 107A of the cylinder and at the same time the fluid (or some other media) is fed to the second side 107B of the piston 107. The feeding is done under the control of the control unit 105.

The device may also comprise a pressure accumulator 109, as is illustrated in an exemplary FIG. 4. The pressure accumulator 109 can apply additional closing force or counterforce via the actuating device 104 for example feeding additional fluid or pressure to either side 107A, 107B of the piston 107 advantageously under a control of the control unit 105. For example the jaws 101, 102 can be moved farther from each other by feeding pressure from the pressure accumulator 109 to the first side 107A of the piston 107 and thereby increasing the counterforce and at the same decreasing the external pressure applied by the jaws 101, 102 on the surface of the object.

The device may also comprise a pressure and/or force sensor 110 for determining pressure and/or force by which the jaws 101, 102 are pressed against the anatomical object. The device may also comprise a flow rate or flow velocity measuring device 111, such as an infrared sensor or ultrasound sensor, for determining flow rate or flow velocity of the fluid flowing inside said anatomical object. In addition the device may also comprise an opening measurement device 118 for measuring a distance between the jaws 101, 102 or the opening angle α of the jaws 101, 102. The pressure and/or force sensor 110 as well as flow rate or flow velocity measuring device 111 and the opening measurement device 118 are advantageously in a data communication with the control unit 105, which can use the determined pressure and/or force information, as well as flow rate or velocity information and other information as a control parameter to control the actuating device 104 to apply the counterforce so that the external pressure applied by the jaws 101, 102 on the surface of the anatomical object, such as the blood vessel, is applied in a way to manipulate the flow rate of the fluid circulation in the anatomical object in a controlled manner, and advantageously determined or predetermined manner.

The device may also comprise a transmitter and/or receiver or transceiver 112 to transfer information related to control unit or control parameters or determined pressure, compressing force or distance information about the distance between the jaws (so diameter or thickness of the anatomic object between the jaws) or information about the opening angle of the jaws outside the device, as well as for receiving data outside the device, such as receiving control data to be used by the control unit for controlling the operation of the actuating device. The data communication between the transmitter, receiver or transceiver 112 and an external device can be implemented either in a wired such as by thin conductor wire or optical fiber conducted through the skin of the patient, or in a wireless way, such as using a short range radio frequencies or infrared especially when the transceiver 112 is just under the skin.

The device may also comprise a memory device 113 to store e.g. control data so that the control unit 105 has access to the memory device and the data stored thereon. The control data or other information may be stored to the memory device 113 either beforehand or it may be transmitted to the memory device also afterwards by the communication methods described elsewhere in this document. The control unit 105 can also store data measured e.g. by the pressure and/or force sensor 110 as well as flow rate or flow velocity measuring device 111 and the opening measurement device 118 to the memory or the memory device 113. The control data or other information may be permanently stored or it can be rewritten.

The device may also comprise a clockwork device 114 providing a timing parameter to the control unit 105 to control e.g. actuating parameters of the actuating device 104 according to the timing parameter and possibly together with other control parameters, and thereby controlling the closing parameters of the device, such as the closing speed and time of the jaws so that the external pressure applied by the jaws on the surface of said anatomical object manipulates the flow rate of fluid circulation in the anatomical object as a function of time according to the timing parameter provided by the clockwork device.

Still in addition the distal end 101A, 102A of at least one of the jaw 101, 102 may be curved or it comprises a serrated or friction surface so to prevent the anatomical object to slip away between the jaws 101, 102. The distal end 101A, 102A of at least one of the jaw 101, 102 may also comprise a hole 119 to allow to stich at least a portion of the anatomical object to the device in order to prevent the anatomical object to slip away between the jaws.

Figure 5:
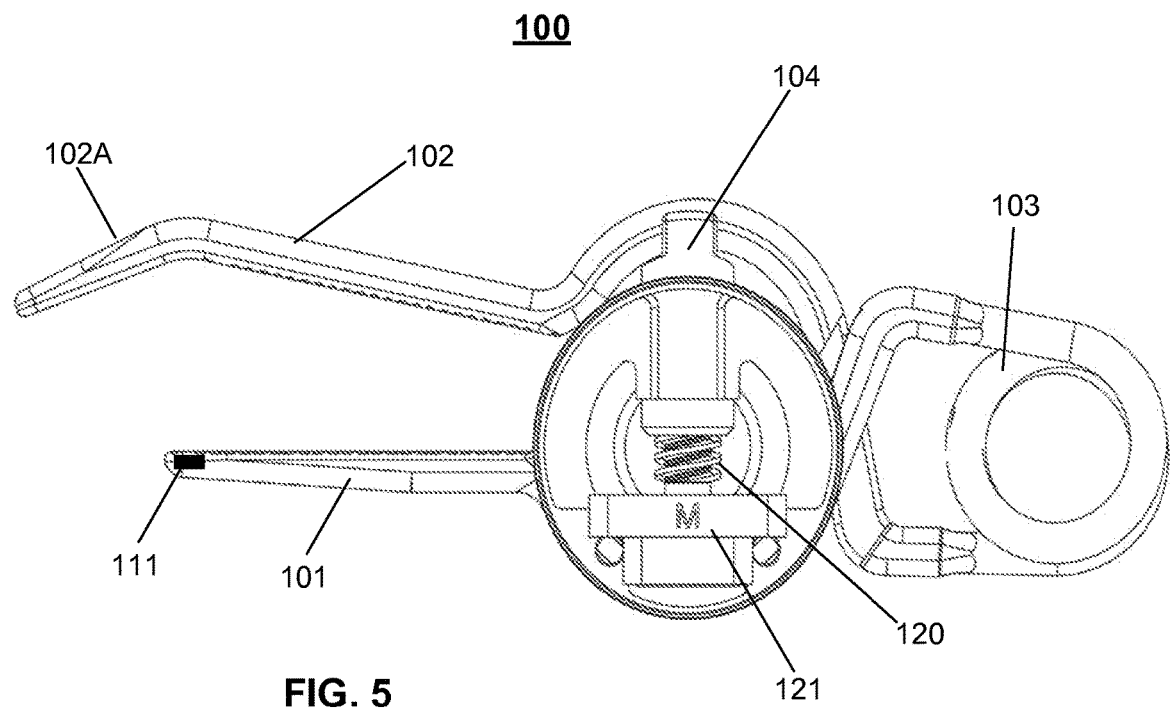
FIG. 5 illustrates still another exemplary device according to an advantageous embodiment of the invention.
Figure 6:
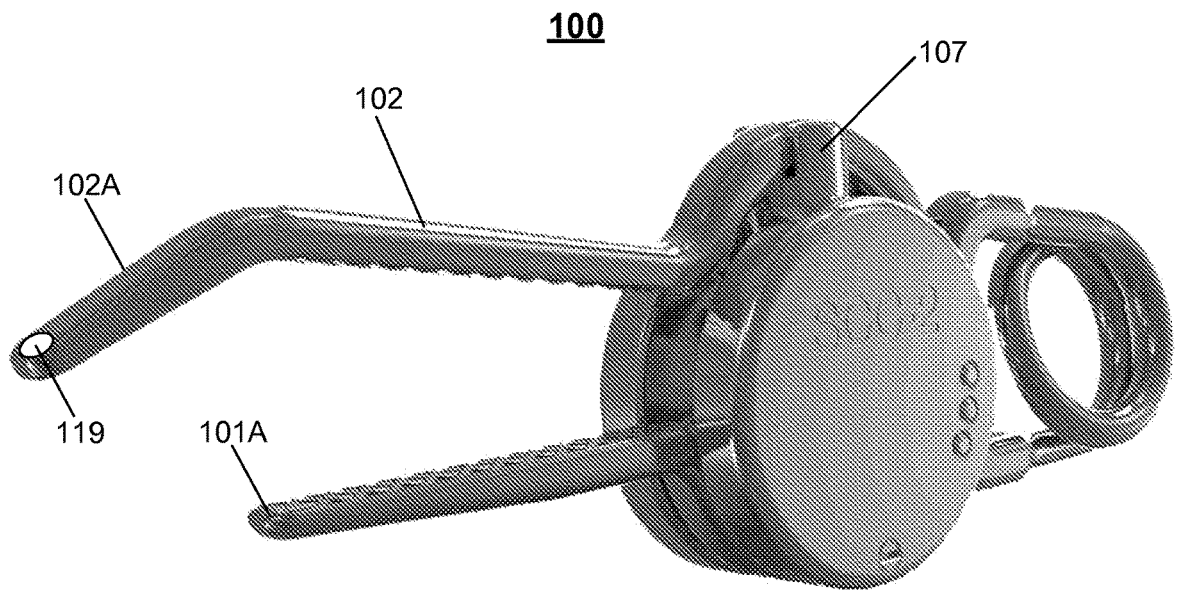
FIG. 6 illustrates a perspective view of an exemplary device according to an advantageous embodiment of the invention.

FIG. 5 illustrates an exemplary device 100 according to an advantageous embodiment of the invention, where the actuating device 104 for applying counterforce against the compressive force is implemented by a screw or threaded rod 120, which is mechanically coupled to at least one of the jaws 101, 102 to apply the counterforce so that the external pressure applied by the jaws on the surface of the anatomical object is applied in a way to manipulate, such as decrease or increase, the flow rate of the fluid circulation in the anatomical object in a controllable manner under the control of the control unit 105. The screw or threaded rod 120 is driven by an electrically driven motor 121, the operation of which is controlled by the control unit 105. Advantageously the screw or threaded rod 120 can be driven both directions and thereby applying either counterforce against the compressive force or additional compressive force. The device 100 illustrated in FIG. 5 naturally comprises also the functions, sensors and other means depicted in connection with another Figures, such as the pressure and/or force sensor 110, transceiver 112, memory device 113, clockwork device 114 and opening measurement device 118.

The device advantageously comprises also a power source 116, such as a battery, and power source cover 117. The device comprises also an actuator cover 115.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims.

For example even if the device of the invention is very suitable for applying external pressure on a surface of an artery and thereby changing hemodynamic stress of the artery and again to treatment of dolichoectatic basilar trunk aneurysms, the device can be applied as well to fluid manipulation of other anatomical objects also.

In particularly it is to be noted that the device according to embodiments of the invention can be used for applying external pressure on anatomical objects having anatomic fluid channels, such as blood vessels or intestine, the flow of which should be manipulated or even prevented completely during or after the operation. For example the external pressure can be applied by the device on a blood vessel in a brain, as is discussed in this document elsewhere, but also in other anatomical object and thereby changing hemodynamic stress and hemodynamic flow by changing arterial or venous diameter to achieve wanted hemodynamic changes in arterial and venous system. The device can be used e.g. for treatment of vascular anomalies, such as a dolichoectatic aneurysm, arteriovenous malformation, dural arteriovenous fistula or fusiform aneurysm, by applying external pressure and thereby isolating from the blood circulation or, at least, reducing the flow and flow-induced mechanical stress in the vascular anomaly, such as in the aneurysm sac.

The features recited in dependent claims are mutually freely combinable unless otherwise explicitly stated.

The invention claimed is:

1. A device for applying external pressure on a surface of an anatomical object, such as a blood vessel, the device comprises:
    at least two jaws,
    a closing force generating device for applying compressive force to the jaws to drive said jaws against each other,
    an actuating device for applying counterforce against said compressive force, and
    a control unit wherein
    said control unit is configured to control said actuating device to apply said counterforce so that said external pressure applied by said device on the surface of said anatomical object manipulates a flow rate of a fluid flow in said anatomical object as a function of time in a controllable manner.

2. The device of claim 1, wherein the closing force generating device comprises a spring, which is configured to apply said compressive force to the jaws to drive said jaws against each other.

3. The device of claim 1, wherein the actuating device comprises a cylinder and piston, where said piston is arranged to apply said counterforce, and wherein said cylinder comprises fluid inside said cylinder to prevent said piston to from moving freely inside the cylinder, and wherein said control unit is configured to remove said fluid from the cylinder in a controlled manner and thereby allowing said piston to be retreated inside the cylinder thereby decreasing the counterforce and allowing said jaws to be driven against each other in a controlled manner.

4. The device of claim 3, wherein the device comprises a valve, whereupon the control unit is configured to control the operation of said valve and thereby configured to control said removing of said fluid from the cylinder via said valve in a controlled manner.

5. The device of claim 3, wherein the device comprises a screw conveyor arranged in connection of said fluid inside said cylinder, whereupon the control unit is configured to control the operation of said screw conveyor and thereby configured to control said removing of said fluid from the cylinder by using said screw conveyor in a controlled manner.

6. The device of claim 3, wherein said cylinder comprises fluid inside said cylinder in both a first and second side of the piston, whereupon said piston is configured to be moved inside the cylinder only if the control unit removes said fluid from the first side of the cylinder and at the same time provides fluid into the second side of the cylinder.

7. The device of claim 1, wherein said actuating device for applying counterforce against said compressive force is an electrically driven motor, which is mechanically coupled to at least one of said jaws to apply said counterforce so that said external pressure applied by said device on the surface of said anatomical object is configured to be applied in a way to manipulate a flow rate of a fluid circulation in said anatomical object as a function of time in a controllable manner.

8. The device of claim 1, wherein the device comprises a pressure accumulator, which is arranged to apply additional counterforce via said actuating device and thereby moving said jaws farther from each other and decreasing said external pressure applied by said device on the surface of said anatomical object.

9. The device of claim 1, wherein the device comprises a pressure or force sensor for determining pressure or force by which said jaws are pressed against the anatomical object, and wherein said device is configured to use said determined pressure or force information as a control parameter of the control unit to control said actuating device to apply said counterforce so that said external pressure applied by said device on the surface of said anatomical object is applied in a way to manipulate a flow rate of the fluid circulation in said anatomical object as a function of time in a controllable manner.

10. The device of claim 1, wherein the device comprises a flow rate measuring device for determining flow rate of the fluid flowing inside said anatomical object, and wherein said device is configured to use said determined flow rate information as a control parameter of the control unit to control said actuating device to apply said counterforce so that said external pressure applied by said device on the surface of said anatomical object is applied in a way to manipulate the flow rate of the fluid circulation in said anatomical object as a function of time in a controllable manner.

11. The device of claim 1, wherein the device comprises a transmitter to transmit information related to the control unit, control parameters, or pressure or force sensor information of pressure or force by which said device is pressed against the anatomical object.

12. The device of claim 1, wherein the device comprises a memory device comprising or configured to receive control data so that said control unit is configured to control actuating parameters of said actuating device according to said control data, and thereby controlling closing parameters of said device so that said external pressure applied by said device on the surface of said anatomical object manipulates the flow rate of the fluid circulation in said anatomical object as a function of time according to said control data.

13. The device of claim 12, wherein the closing parameters comprise closing speed and time of the jaws, and wherein said manipulating comprises decreasing the flow rate of the fluid circulation in said anatomical object as a function of time according to said control data.

14. The device of claim 1, wherein the device comprises a clockwork device providing a timing parameter to said control unit to control actuating parameters of said actuating device according to said timing parameter, and thereby controlling closing parameters of said device so that said external pressure applied by said device on the surface of said anatomical object manipulates the flow rate of fluid circulation in said anatomical object as a function of time according to said timing parameter provided by said clockwork device.

15. The device of claim 1, wherein the device comprises a memory device and a receiver device for receiving data outside the device, said received data comprising control data to be used by the control unit for controlling operation of said actuating device.

16. The device of claim 1, wherein the device comprises a self-reset function for resetting parameters.

17. The device of claim 1, wherein the device comprises a communication device for receiving control commands outside the device for applying control data to said control unit to control said actuating device to apply said counterforce so that said external pressure applied by said device on the surface of said anatomical object is applied in a way to manipulate a flow rate of the fluid circulation in said anatomical object as a function of time in a controllable manner.

18. The device of claim 1, wherein a distal end of at least one of the at least two jaws is curved or comprises a serrated or friction surface to prevent the anatomical object from slipping out from between the jaws as the device applies external pressure on the surface of the anatomical object.

19. The device of claim 1, wherein at least one of the at least two jaws comprises a hole to allow stitching of at least a portion of the anatomical object to said device in order to prevent said anatomical object to from slipping out from between the jaws as the device applies external pressure on the surface of the anatomical object.

20. The device of claim 1, wherein the device comprises titanium in order to prevent the device from interfering with MRI scanning.

21. The device of claim 1, wherein the compressive force applied to the jaws to drive the jaws against each other is in the range of 0.1-50 N.

* * * * *